United States Patent [19]

Lin et al.

[11] Patent Number: 5,251,468

[45] Date of Patent: Oct. 12, 1993

[54] METHOD OF SURFACE FINISHING ORTHOPAEDIC IMPLANT DEVICES USING A BIOACTIVE BLASTING MEDIUM

[75] Inventors: Steve T. Lin, Ft. Wayne; Mike Hawkins, Columbia City; Steve Krebs, Fort Wayne, all of Ind.

[73] Assignee: Zimmer, Inc., Warsaw, Ind.

[21] Appl. No.: 990,207

[22] Filed: Dec. 14, 1992

[51] Int. Cl.$^5$ .......................... B24C 1/00; A61F 5/04
[52] U.S. Cl. .......................... 72/53; 51/320; 29/90.7; 606/53
[58] Field of Search ...................... 72/53; 51/319, 320; 29/90.7

[56] References Cited

U.S. PATENT DOCUMENTS

| | | | |
|---|---|---|---|
| 3,090,166 | 5/1963 | Straub | 51/320 |
| 3,702,519 | 11/1972 | Rice et al. | 51/320 |
| 3,895,465 | 7/1975 | Korn et al. | 51/320 |
| 5,057,108 | 10/1991 | Shetty et al. | 72/53 |
| 5,063,015 | 11/1991 | Lloyd et al. | 51/320 |
| 5,112,406 | 5/1992 | Lajoie et al. | 51/320 |

Primary Examiner—David Jones
Attorney, Agent, or Firm—Todd A. Dawson

[57] ABSTRACT

The method and material of this invention eliminates the necessity of removing imbedded particles remaining after shot blasting by providing a method for surface finishing an orthopaedic implant wherein the blasting medium is bioactive. The surface finishing with bioactive material may also be used to clean the porous surface after sintering or diffusion bonding. Since the particles are made from bioactive material, it is not a concern if particles remain in the porous surface after blasting.

2 Claims, 2 Drawing Sheets

METHOD OF SURFACE FINISHING ORTHOPAEDIC IMPLANT DEVICES USING A BIOACTIVE BLASTING MEDIUM

FIELD OF THE INVENTION

The present invention relates to orthopedic implant devices and, more particularly, to a surface treatment process applicable to such devices to enhance the fatigue and corrosion properties wherein the blasting medium is bioactive. The shot blasting method using a bioactive coating is also applicable to surface cleaning of orthopaedic implants including those with porous surfaces.

BACKGROUND OF THE INVENTION

A variety of metal alloys are used for orthopaedic implants and are chosen on the basis of the high strength, ductility, fracture toughness, biocompatability, and corrosion resistance. It is generally known that the fatigue and corrosion properties of orthopedic implant devices fabricated from these alloys can be affected by different surface treatment processes including shot blasting. Recently, orthopaedic implant devices have been surface treated by shot blasting with alumina, in the form of aluminum oxide having a hard crystalline structure. Glass shot is also being used as a blasting medium as well as stainless steel shot. The problem with shot blasting orthopaedic components is that the blasted substances tend to become imbedded in and/or leave a residue on the surface of some alloys therefore requiring subsequent steps of glass bead blasting and electropolishing. Since the contamination by the blasting medium must be substantially removed, the depth of the cold worked outer layer formed by the blasting is limited. One method for increasing the depth of the cold worked outer layer is described and claimed in U.S. Pat. No. 5,057,108 issued on Oct. 15, 1991 entitled: METHOD OF SURFACE FINISHING ORTHOPEDIC IMPLANT DEVICES. As claimed, the '108 patent calls for the shot blasting of the outer surface with metal shot followed by blasting with a glass bead and electropolishing.

When porous surfaces, such as fiber metal mesh or metal beads, are either diffusion bonded or sintered to the body of an orthopaedic implant, it is known to use a carbon tool to hold pressure against the porous surface. The problem is that during the process, small pieces of carbon may become attached to the porous surface. This carbon must be cleaned off of the porous surface.

SUMMARY OF THE INVENTION

The method and material of this invention provides a solution to the above problems of removing imbedded particles remaining after shot blasting by providing a method for surface finishing an orthopaedic implant wherein the blasting medium is bioactive. The surface finishing with bioactive material may also be used to clean the porous surface after sintering or diffusion bonding. Since the particles are made from bioactive material, it is not a concern if particles remain in the porous surface after blasting.

Calcium phosphate ceramics have recently seen clinical use as bone substitute materials and as coating for total joint prostheses. The two most common calcium phosphate ceramics used are tricalcium phosphate and hydroxyapatite. When placed in hard tissue sites, hydroxyapatite and tricalcium phosphate provide an osteophilic scaffolding on which bone can proliferate and to which it can bond chemically. Tricalcium phosphate is bioabsorbable. Hydroxyapatite is relatively insoluble.

Phosphate glass compositions which are intended to be absorbable in the body have been investigated in animals in the formation of bone screws and other types of fracture fixation means.

As used in this invention, the term bioactive will refer to calcium phosphate ceramics, phosphate glass compositions, bioabsorbable glass, partially absorbable glass, bioceramics (either totally bioabsorbable, partially absorbable, or non-absorbable). These known bioactive materials are available in the industry in a variety of hardness to serve a variety of uses.

The use of a bioactive blasting medium greatly reduces the need to clean the implant after blasting since any particles remaining in the implant are bioactive and not a detriment to body tissue. Further, since the blast media is bioactive, porous or textured surfaces could be shot blasted for cleaning without worry of contamination of the part.

Accordingly, it is an advantage of the invention to provide a method of surface finishing an orthopaedic implant wherein the surface finishing medium is bioactive.

Another advantage of the invention is to provide for a method of shot blasting an orthopaedic implant to enhance fatigue properties of the implant, wherein the blasting medium is bioactive.

Another advantage of the invention is to provide for a method of shot blasting an orthopaedic implant to enhance fatigue properties of the implant, wherein the blasting medium is formed from a calcium phosphate ceramic.

Another advantage of the invention is to provide for a method of shot blasting an orthopaedic implant to enhance fatigue properties of the implant, wherein the blasting medium is formed from a phosphate glass composition.

Yet another advantage of this invention is to provide for a method of cleaning a porous surface on an orthopaedic implant using a bioactive material.

Still other advantages of the invention will become apparent upon a reading of the following description taken with the accompanying drawings.

DESCRIPTION OF THE PREFERRED EMBODIMENTS

The preferred embodiments herein described are not intended to be exhaustive or to limit the invention to the precise forms disclosed. Rather, they are chosen and described to best explain the invention so that others skilled in the art might utilize their teachings.

Figure 1:
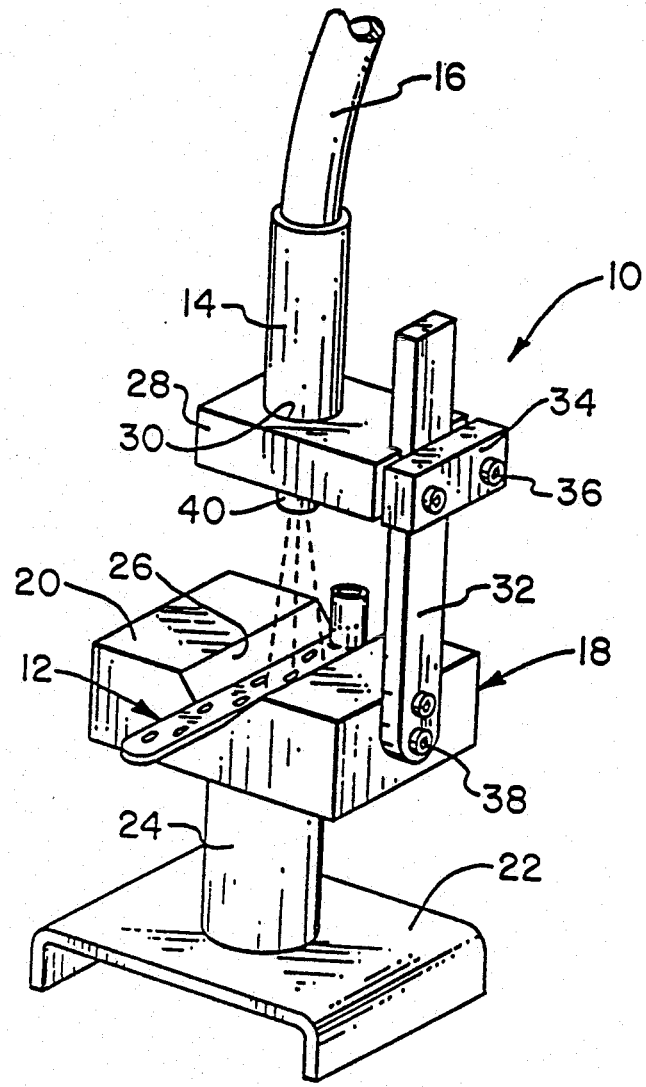
FIG. 1 is a perspective view of the spray nozzle and fixture associated with a shot blasting apparatus of the type used in accordance with the method of the present invention, wherein a fixation plate is shown being processed.

Referring now to FIG. 1, there is shown a shot blasting nozzle and fixture assembly 10 of the type used in conjunction with a shot blasting apparatus (not shown) in carrying out the process and producing an orthopaedic implant device 12 in accordance with the present invention. Assembly 10 includes a nozzle 14 used to carry and expel blasting media, i.e., calcium phosphate ceramic beads and phosphate glass composition beads. Nozzle 14 is connected to a hose 16, which is operably connected to a dry blast system, such as a Model 4228-F system manufactured by Cyclo-Blast Dry Honer Co. of Belmont, Calif.

Assembly 10 also includes a fixture 18 for supporting a work piece, i.e., orthopaedic implant device 12, during the shot blasting steps of the present invention described below. Fixture 18 includes a support block 20 attached to a base member 22 by means of a neck portion 24. As illustrated in FIG. 1, the top surface of support block 20 includes a V-shaped groove 26 in which device 12 is disposed during the shot blasting operations. Nozzle 14 is selectively spaced above support block 20 by means of a horizontal plate member 28 having an opening 30 through which nozzle 14 is operably received and retained therein.

Plate member 28 is slidably connected to a vertical spacing bar 32, for selective positioning above support block 20, by means of a clamping block 34 and a pair of screws 36. Spacing bar 32 is fixedly mounted to support block 20 by a pair of screws 38. Accordingly, it can be seen from FIG. 1 that a nozzle opening 40 of nozzle 14, from which blasting media is expelled by high pressure air, is directed toward and selectively positioned above the work piece resting on support block 20.

Figure 2:
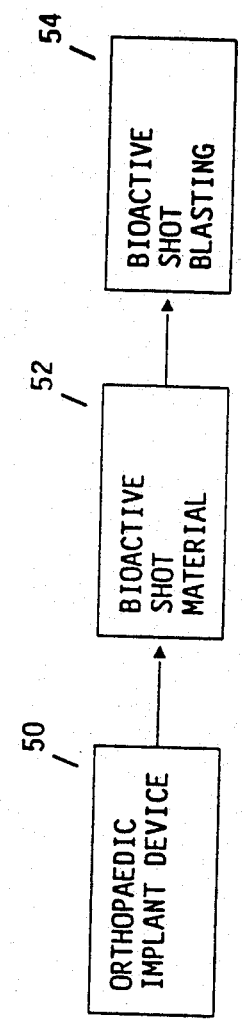
FIG. 2 is a diagrammatic representation of the process steps involved in an exemplary embodiment of the method of the present invention.

Referring now to FIG. 2, the steps for surface treating a stainless steel orthopaedic implant device in accord with an exemplary embodiment of the present invention are diagrammatically illustrated. Generally, block 50 represents the first step of providing an orthopaedic implant device or a component part thereof, i.e., a metal substrate.

Block 52 represents providing a bioactive shot material. The bioactive shot is from a list of known compositions that are not inert within the body and are not detrimental to the surrounding body tissue. For example, the bioactive shot could be formed from any of the following: calcium phosphate ceramics, phosphate glass compositions, bioabsorbable glass, partially absorbable glass, bioceramics (either totally bioabsorbable, partially absorbable, or non-absorbable). This listing should not be considered exhaustive but merely an illustration of the materials available and known which would be considered bioactive materials within the keeping of the invention and which may be used as a blasting media. The bioactive shot may be of any particular geometry which is used in standard blast equipment such as spherical, cuboidal, or random. The particular material used may depend on the specific use of the implant. For example, if a porous surfaced implant intended for bone ingrowth is being treated, it may be desirable to use hydroxyapatite as a blasting media to further enhance bone growth. No matter what material is used, it should be formed with a mass sufficient to allow blasting with relatively normal velocities for shot blasting.

Block 52 represents the next step of shot blasting the outer surface of the part with bioactive shot.

The metal substrate provided in the step of block 50 is preferably hot forged or cold-worked 22Cr-13Ni-5Mn (22-13-5) stainless steel alloy (Rb 60 to Rc 50), or hot forged or cold-worked 316L stainless steel alloy (Rb 60 to Rc 50). Both are used in fracture fixation devices due to their high strength ductility, fracture toughness, biocompatability, and corrosion resistance. Inasmuch as the substrate has already been fabricated into an orthopedic implant component part prior to this step, the surface has been appropriately machined, surface ground, and/or mass tumbled.

The step of block 52 involves providing a bioactive material of sufficient size and mass to distort the work piece in a manner consistent with shot blasting. An example list of the type of bioactive materials suitable for this application may be found above.

The step of block 54 involves shot blasting the work piece with bioactive shot.

The time duration for shot blasting with the bioactive material to achieve thorough coverage of the target area varies according to several variables, including the type of material and target materials, the size, shape, hardness and density of the shot, and the velocity, flow rate, and angle of impact. All these variables and the manner in which they are controlled to obtain the desired surface finish are well known in the art.

Further, it is known in the art that metals having a cold worked outer layer exhibit enhanced fatigue properties.

It should be understood upon reading the above that when the surface finishing is complete, any blasting residue remaining on the surface of the implant will be from the bioactive blasting material and therefore is not detrimental to human tissue. Therefore, glass bead blasting to clean the residue from the implant is not necessary, thereby reducing production costs to the manufacturer.

The method of the invention is applicable to the cleaning of an orthopaedic implant having a textured or porous surface. When the method of the invention and the blasting media of the invention are used for the purpose of cleaning an orthopaedic implant, the velocities at which the bioactive material is shot out and the hardness of the bioactive material will be reduced so as not to effect the structure of the implant. When used in this manner, it is inevitable that small particles of the bioactive blasting material will remain in the porous surface after blasting. Since the material is bioactive, any residue left by the process will not be a detriment to human tissue. Use of the bioactive coating as a cleaning material eliminates also the need for further cleaning steps on the part of the manufacturer and thereby reduces costs.

It should be understood that the method and material of the invention should not be limited to the precise forms disclosed but may be modified within the scope of the appended claims.

We claim:

1. A method of surface finishing an orthopaedic implant device, the method comprising the steps of:
   a) providing a metal substrate in the form of an orthopaedic implant device with an outer surface;
   b) providing a bioactive shot formed from a bioactive material; and
   c) shot blasting said outer surface of said metal substrate with said bioactive about, wherein said bioactive material is from the group of calcium phosphate ceramics, phosphate glass compositions, bioabsorbable glass, partially absorbable glass, totally bioabsorbable bioceramics, partially bioabsorbable bioceramics, non-absorbable bioceramics.

2. A blasting material used in surface finishing of orthopaedic implants, wherein the blasting material is bioactive, and is from the group of calcium phosphate ceramics, phosphate glass compositions, bioabsorbable glass, partially absorbable glass, totally bioabsorbable bioceramics, partially bioabsorbable bioceramics, and non-absorbable bioceramics.

* * * * *